US00PP22403P3

(12) United States Plant Patent
Bacon

(10) Patent No.: US PP22,403 P3
(45) Date of Patent: Dec. 27, 2011

(54) PLUM TREE NAMED 'SUPLUMFORTYTWO'

(50) Latin Name: *Prunus salicina*
Varietal Denomination: Suplumfortytwo

(75) Inventor: Terry Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 124 days.

(21) Appl. No.: 12/657,362

(22) Filed: Jan. 19, 2010

(65) Prior Publication Data

US 2011/0179535 P1 Jul. 21, 2011

(51) Int. Cl.
*A01H 5/00* (2006.01)

(52) U.S. Cl. ..... Plt./184

(58) Field of Classification Search ..... Plt./184
See application file for complete search history.

(56) References Cited

U.S. PATENT DOCUMENTS

| | | | | |
|---|---|---|---|---|
| PP9,858 | P | 4/1997 | Zaiger et al. | |
| PP19,630 | P3 * | 1/2009 | Russell et al. | Plt./184 |
| PP21,864 | P2 * | 4/2011 | Bacon | Plt./184 |

* cited by examiner

*Primary Examiner* — Wendy C Haas
(74) *Attorney, Agent, or Firm* — Knobbe, Martens, Olson & Bear, LLP

(57) ABSTRACT

A new and distinct plum tree variety, *Prunus salicina,* cv. 'Suplumfortytwo' is characterized by large fruit with black skin.

1 Drawing Sheet

Latin name of the genus and species claimed: *Prunus salicina.*

Variety denomination: 'Suplumfortytwo'.

BACKGROUND AND SUMMARY OF THE INVENTION

This invention relates to the discovery and asexual propagation of a new and distinct variety of plum, *Prunus salicina* cv. 'Suplumfortytwo'. The new variety was first hybridized in 2001 and selected in 2003 by Terry Bacon as breeder number: 'PL264YB'. The new variety was first evaluated by Terry Bacon near Wasco, Calif. in Kern County. The variety 'Suplumfortytwo' was originated by hybridization.

The new variety 'Suplumfortytwo' is characterized by large fruit with black skin.

The seed parent is '90P-059' (unpatented), and the pollen parent is an unknown plum in the breeding population. The parent varieties were first crossed in March of 2001, with the date of planting of the progeny being February 2002, and the date of first flowering being February 2003. The new plum variety 'Suplumfortytwo' was first asexually propagated by Terry Bacon near Wasco, Kern County, Calif. in January 2007, by budding.

The new variety 'Suplumfortytwo' is distinguished from its seed parent, '90P-059' (unpatented), in that the new variety has black skin while '90P-059' has yellow skin.

The new variety 'Suplumfortytwo' has a similar ripening time as 'Black Amber' (unpatented), but the fruit diameter is larger at 70 mm perpendicular to the suture, while 'Black Amber' is about 60 mm. The new variety 'Suplumfortytwo' has a similar ripening time as 'Hiromi Red' (U.S. Plant Pat. No. 9,858), but the skin is black colored compared to 'Hiromi Red', which has red skin.

The new variety 'Suplumfortytwo' has been shown to maintain its distinguishing characteristics through successive asexual propagations by, for example, budding.

BRIEF DESCRIPTION OF THE PHOTOGRAPH

The accompanying color photographic illustration shows typical specimens of the foliage and fruit of the present new plum variety 'Suplumfortytwo'. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England 1986.

The descriptive matter which follows pertains to 4 year old 'Suplumfortytwo' plants on Nemared (unpatented) rootstock, grown in the vicinity of Wasco, Kern County, Calif., during 2009, and is believed to apply to plants of the variety grown under similar conditions of soil and climate elsewhere.

TREE

General: (Measurements taken on 4 year old tree unless otherwise noted.)

*Size.*—Medium. Normal for most plum varieties. Reaches a height of approximately 3 meters with normal pruning.
*Spread.*—Normal for most plum varieties. Approximately 3 meters.
*Vigor.*—Moderately vigorous.
*Growth.*—Spreading.
*Productivity.*—Productive.
*Form.*—Vase formed.
*Bearer.*—Regular.
*Fertility.*—Requires pollination to set a full crop.
*Canopy density.*—Medium-dense.
*Hardiness.*—Hardy in all fruit growing areas of California. Winter chilling requirement is approximately 250 hours at or below 7.2 C.
*Disease resistance/susceptibility.*—No specific testing for relative plant disease resistance/susceptibility has been undertaken. Under close observation in Kern County, Calif., no particular plant/fruit disease resistance/susceptibility has been observed.

Trunk: (Measurements at approximately 30 cm above soil line.)
*Diameter.*—Approximately 13 cm, varies with soil type, fertility, climatic conditions and cultural practices.
*Texture.*—Medium shaggy, increases with age of tree.
*Trunk color.*—About Light Greyed-green 198B to Medium Greyed-orange 173B; becomes darker with age.

Branches: (Measurements at approximately 90 cm above soil line.)
*Size.*—Diameter ranges from approximately 8 cm.
*Texture.*—Medium, shaggy.
*Color.*—Varying between about Light Greyed-green 198B to Medium Greyed-orange 173B; becomes darker with age.
*Number of Lenticels.*—Absent.

Flowering shoots: (Data taken in July at midpoint of previous season shoots.)
*Size.*—Average diameter approximately 6 mm.
*Color.*—Topside: About Dark Greyed-orange 172A to Medium Greyed-orange 172C. Underside: About Dark Greyed-orange 172A to Medium Greyed-orange 172C.
*Internode length.*—Medium; approximately 1-4 cm. Midway on flowering shoot.
*Flowering shoot lenticels.*—Medium. Color: About Light Greyed-green 198B. Diameter: Approximately 0.2 mm.
*Flowering shoot leaf buds.*—Shape: Conical. Width: Approximately 2 mm. Length: Approximately 3 mm. Color: About Dark Greyed-orange 176A.
*Flowering shoot flower buds.*—Shape: Conical. Width: Approximately 1.5 mm. Length: Approximately 2 mm. Color: About Dark Greyed-orange 176A. Number of buds per node: Usually 2-3.
*Density of buds.*—Medium.
*Flower bud distribution.*—Generally on spurs and one year old shoots and older wood.
*Ratio of wood (leaf) buds to flowering buds.*—1/2.

FOLIAGE

Leaves:
*Size.*—Medium.
*Average length.*—Medium; approximately 90 mm without petiole.
*Average width.*—Medium; approximately 35 mm.
*Thickness.*—Medium.
*Color.*—Upper surface: About Dark Green 137B. Lower surface: About Dark Green 138B.
*Form.*—Broad, obovate.
*Tip.*—Cuspidate.
*Base.*—V-shaped.
*Margin.*—Crenate.
*Venation.*—Pinately veined.
*Vein color.*—About Light Green 139D on lower surface.
*Surface texture.*—Smooth.
*Leaf blade (ratio of length to width).*—Medium, about 2.6 to 1.
*Shape in the cross section.*—Concave.
*Profile.*—Up folded.
*Leaf blade tip.*—Curved downwardly.
*Undulation of margin.*—Slight.

Petiole:
*Average length.*—Medium; approximately 11 mm.
*Average diameter.*—Approximately 2 mm.
*Color.*—About Light Green 139D.
*Thickness.*—Medium, approximately 2 mm.

Stipules:
*Number/leaf bud.*—Approximately 2.
*Typical length.*—Approximately 7 mm.
*Color.*—About Dark Greyed-orange 176A when dry.
*Persistence.*—Falls off.

Leaf glands:
*Form.*—Reniform.
*Average number.*—Usually 0-4.
*Position.*—On both leaf base and petiole, opposite.
*Average size.*—Small; approximately 1 mm.
*Color.*—About Dark Greyed-orange 176A.

FLOWERS

General:
*Flower blooming period.*—First bloom: Approximately Feb. 10, 2009. Full bloom: Approximately Feb. 17, 2009.
*Time of bloom.*—Early.
*Duration of bloom.*—Medium; approximately 10 days.
*Diameter of fully opened flower.*—Medium, approximately 20 mm.
*Flower aroma.*—Slight aroma.
*Shape.*—Rosaceous.

Peduncle:
*Length.*—Medium; approximately 12 mm.
*Diameter.*—Slender; approximately 1.5 mm.
*Color.*—About Yellow-green 144B.
*Pubescence.*—Absent.

Petals:
*Number.*—5.
*Arrangement.*—Overlapping slightly.
*Length.*—Approximately 10 mm.
*Diameter.*—Approximately 7 mm.
*Shape.*—Obovate.
*Apex shape.*—Rounded.
*Base shape.*—Narrows at point of attachment.
*Color.*—White.
*Surface texture.*—Smooth.
*Margins.*—Slightly undulating, entire.
*Claw length.*—Medium.

*Margin waviness.*—Medium.
*Base angle.*—Narrow.
*Division of upper margin.*—Entire.
*Pubescence of inner surface.*—Absent.
*Pubescence of outer surface.*—Absent.

Sepals:
*Number.*—5.
*Length.*—Approximately 3 mm.
*Diameter.*—Approximately 3 mm.
*Shape.*—Triangular.
*Color.*—About Yellow-green 144A.
*Surface texture.*—Smooth.
*Margins.*—Entire.
*Positioning.*—Adpressed to petals.
*Pubescence of inner surface.*—Absent.
*Pubescence of outer surface.*—Absent.

Stamens:
*Number.*—Ranges from approximately 27 to approximately 30.
*Average length.*—Approximately 4-10 mm.
*Filament color.*—About white.
*Anther color.*—About Medium Greyed-yellow 162A.
*Flower pollen color.*—About Medium Greyed-yellow 162A when dried.
*Position.*—Perigynous.

Pistil:
*Number.*—Usually one, occasionally two.
*Average length.*—Approximately 8-10 mm.
*Ovary diameter.*—Approximately 1 mm.
*Pubescence.*—None.
*Stigma extension in comparison to anthers.*—Usually below.
*Style frequency of supplementary pistils.*—Few.

Receptacle:
*Depth.*—Medium.
*Pubescence of inner surface.*—Absent.
*Pubescence of outer surface.*—Absent.

FRUIT

General: (Description taken near Wasco, Kern County, Calif.)
*Harvest.*—
*Date of first pick.*—Approximately Jun. 17, 2009.
*Date of last pick.*—Approximately Jun. 27, 2009.

Maturity when described: Firm-mature.
Season ripening: Early-medium.
Position of maximum diameter: Towards the middle.
Symmetry about the suture: Symmetric.

Size:
*Length* (*stem end to apex*).—Approximately 60 mm.
*Diameter in line with suture plane.*—Approximately 60 mm.
*Diameter perpendicular to suture plane.*—Approximately 70 mm.
*Average weight.*—Approximately 136 gm.

Form:
*Viewed from apex.*—Rounded, nearly symmetrical.
*Viewed from side, facing suture.*—Rounded, nearly symmetrical.
*Viewed from side, perpendicular to suture.*—Rounded, nearly symmetrical.

Apex shape: Rounded.

Fruit stem cavity:
*Shape.*—Rounded.
*Depth.*—Medium; Approximately 0.5 cm.
*Breadth.*—Approximately 2-3 cm.
*Width.*—Medium, approximately 2-3 cm.

Fruit stem:
*Length.*—Medium; approximately 9 mm.
*Diameter.*—Approximately 3 mm.
*Color.*—About 147D.
*Adherence to stone.*—Medium.

Fruit skin:
*Thickness.*—Medium.
*Adherence to flesh.*—Very strong.
*Surface texture.*—Smooth-medium.
*Pubescence.*—None.
*Bloom.*—Slight.
*Ground color.*—About Dark Greyed-purple 185A, when visible.
*Overcolor.*—About Dark Greyed-purple 187A to Black 202A.
*Taste.*—Neutral.
*Reticulation.*—Absent.
*Roughness.*—Absent.
*Tenacity.*—Tenacious to flesh.
*Tendency to crack.*—None in wet season.

Flesh:
*Ripens.*—Evenly.
*Texture.*—Fine.
*Fibers.*—Few.
*Flavor.*—Mildly tart-sweet.
*Brix.*—Approximately 17°.
*Juice.*—Abundant.
*Aroma.*—Slight.
*Color.*—About Medium Yellow-orange 23B.
*Acidity.*—Medium.
*Eating quality.*—Good.
*Stone/flesh ratio.*—1/98.
*Firmness.*—Firm.

Pit cavity size:
*Length* (*diameter in line with suture plane*).—Approximately 22 mm.
*Diameter perpendicular to suture plane.*—Approximately 15 mm.
*Color.*—About Medium Yellow-orange 23B.

Fruit use: Fresh market.

Fruit shipping and keeping quality: Good, holds well in cold storage and maintains good firmness and eating quality, minimal bruising and scarring in packing and shipping trials.

Stone: (Measurements taken on dried stones.)
*Stone freeness.*—Cling.
*Degree of adherence to flesh.*—Medium.
*Stone size.*—Size compared to Fruit: Medium. Length (Diameter in line with suture plane): Approximately 22 mm. Diameter perpendicular to suture plane: Approximately 15 mm. Width of Stalk End: Medium; approximately 3 mm. Angle of Stalk end: Right angle. Hilum: Oval.
*Stone form.*—Viewed from side: Nearly rounded, irregular. Viewed from ventral side: Flattened. Viewed from stem end: Oval, nearly symmetric.
*Stone shape.*—Base shape: Nearly straight. Apex shape: Rounded with small point.
*Stone surface.*—Furrowed and pitted irregularly throughout.
*Stone halves.*—Nearly equal.
*Stone ridges.*—Rough and irregular.
*Stone outgrowing keel.*—Well-developed.

*Stone tendency to split.*—None.
*Stone color.*—About Light Orange 28C.
*Position of maximum.*—Toward middle.
*Ventrical edge.*—Narrow.
*Dorsal edge.*—Narrow, continuous.

What is claimed is:

1. A new and distinct plum tree as herein described and illustrated.

* * * * *

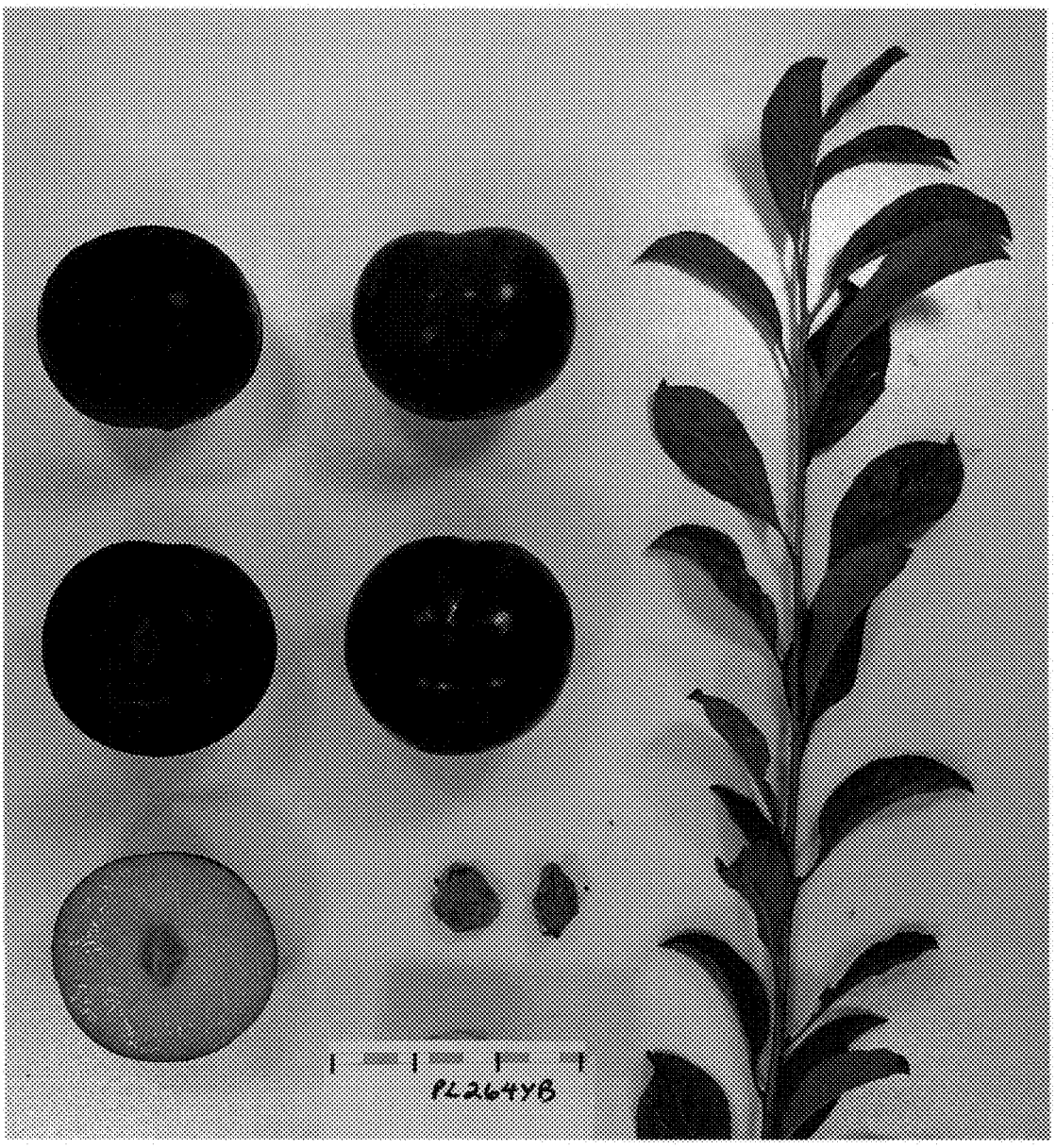
PL264YB